(12) United States Patent
Rappette et al.

(10) Patent No.: US 6,178,254 B1
(45) Date of Patent: Jan. 23, 2001

(54) METHOD FOR ELIMINATION OF EFFECTS OF IMPERFECTIONS ON COLOR MEASUREMENTS

(75) Inventors: Jeffrey P. Rappette, Waukesha; John C. Seymour, Jefferson, both of WI (US)

(73) Assignee: Quad/Graphics, Inc., Sussex, WI (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/087,475

(22) Filed: May 29, 1998

(51) Int. Cl.$^7$ .......................................... G06K 9/00
(52) U.S. Cl. ...................................... 382/112; 250/559.01
(58) Field of Search .................... 382/112, 100; 250/559.01; 348/88

(56) References Cited

U.S. PATENT DOCUMENTS

| | | | |
|---|---|---|---|
| 4,602,291 | 7/1986 | Temes | 358/221 |
| 4,642,684 * | 2/1987 | Alkofer | 358/522 |
| 5,053,866 | 10/1991 | Johnson | 358/75 |
| 5,307,182 * | 4/1994 | Matlz | 358/518 |
| 5,331,420 | 7/1994 | Yamano et al. | 348/246 |
| 5,448,379 | 9/1995 | Ishihara et al. | 358/518 |
| 5,481,380 | 1/1996 | Bestmann | 358/504 |
| 5,509,086 | 4/1996 | Edgar et al. | 382/167 |
| 5,563,717 | 10/1996 | Koeng et al. | 358/406 |
| 5,625,413 | 4/1997 | Katoh et al. | 348/246 |
| 5,649,072 | 7/1997 | Balasubramanian | 395/109 |
| 5,724,259 | 3/1998 | Seymour et al. | 364/526 |
| 5,791,249 * | 8/1998 | Quadracci | 101/450.1 |

* cited by examiner

*Primary Examiner*—Yon J. Couso
(74) *Attorney, Agent, or Firm*—Michael Best & Friedrich LLP (57) ABSTRACT

A method for monitoring the color quality of color patches printed on a web is disclosed. The method includes the steps of using an imaging device to receive light reflected from the printed image on the substrate to produce a signal. The signal is transmitted from the imaging device to a computer and processed in the computer. Processing the signal in the computer includes the steps of digitizing the signal to produce a digitized array of pixels, each pixel having an associated color value, determining a portion of the pixels within the digitized array corresponding to the color patch, determining an acceptable range of color values for the pixels in the portion of the pixels, determining for each pixel in the portion of pixels whether the color value is within the acceptable range, and computing an aggregate color value for the color patch by averaging the color values of each pixel in the portion of pixels including only those color values within the acceptable range.

14 Claims, 4 Drawing Sheets

METHOD FOR ELIMINATION OF EFFECTS OF IMPERFECTIONS ON COLOR MEASUREMENTS

FIELD OF THE INVENTION

The present invention relates generally to monitoring color on a printing press. More particularly, the invention relates to a method for accurately monitoring color, based on measuring the reflectance and/or the optical density of color patches printed on a web, and correcting for the effects of imperfections in the printed color bar patches.

BACKGROUND OF THE INVENTION

In the printing industry, quality control of color printing processes typically has been achieved by measuring the optical density of a test image using a densitometer or scanning densitometer off-line of the web printing process. Optical density measurements are performed by illuminating a test image with a light source and measuring the intensity of the light reflected from the image. Optical density (D) is defined as:

$$D = -\log_{10}(R)$$

where R is the reflectance, or ratio of reflected light intensity to incident light intensity.

The test image which is measured is often in the form of color test strips or color bars. These color bars are comprised of individual color patches of varying ink color and tone having dimensions approximately 0.2 inches by 0.2 inches, with the color patches laid out in a row adjacent one another. The color bars often extend across the width of the web, are printed in the trim area of the web, and may be utilized for registration as well as color monitoring purposes. As printers attempt to minimize paper costs through the use of "short-cutoff" presses (for example, the Harris-Heidelberg M-1000BE or M-3000 press), the trim area on the printed sheet becomes smaller, and accordingly, so do the color patches. The color patches presently may be as small as 0.10 inches by 0.0625 inches.

During the printing process, the color patches will occasionally be printed with imperfections. These imperfections include blemishes caused by a particle of foreign material caught in the ink train, spots caused by ink spray, dropouts of color caused by the blanket cylinder picking paper fiber and ink from the paper, and the overlap of two adjacent patches due to variance in registration. Another imperfection in all patches is caused by scatter within the paper. This causes the edges of a patch with white surrounding it to have a lower measured density than the rest of the patch, irrespective of the ink film thickness. This border effect may exist for approximately 100 microns at the edges of the patch.

In traditional automated color measurement devices, these imperfections will cause measurement errors. Unfortunately, heretofore there has been no reliable method to determine whether the patch has an imperfection. One approach has been to retain only the pixels within the patch having a color value which fits within a predetermined range, while excluding all other pixels having color values outside the range, labelling them invalid. The problems with this method derive from the setting of the predetermined range. If the range is too tight, there is a risk of rejecting legitimate color values. If the range is too wide, there is a risk of accepting color values associated with minor imperfections in the color patch.

One method for the optical density measurement of color patches in a color bar is disclosed in U.S. Pat. No. 5,724,259, issued Mar. 3, 1998. This patent also discloses a method and system for locating the individual color patches in an acquired image and correcting for the effects of scattered light.

SUMMARY OF THE INVENTION

It is an object of the present invention to reliably obtain higher accuracy in color measurements of color patches printed on the web. It is a further object of the invention to provide a method to avoid the rejection of valid pixels within a color patch while at the same time not accepting invalid pixels with color values indicative of minor imperfections. This is accomplished, in general, by sensing the reflectance of the patch at a multiplicity of locations or pixels throughout the patch, and employing techniques to screen these reflectance values for outlying values.

A color video camera is ideal for measuring reflectance and/or optical density on-line because many points can be measured at the same time and precise alignment of the camera with the test area is not necessary. However, optical density measurements of color patches on-line may be inaccurate in part because of the imperfect nature of the printing process and the nature of the web itself. For example, imperfections in the color bar patches lead to inaccurate optical density measurements which are not wholly reflective of the true ink colors. Better accuracy can be obtained by identifying the imperfections and eliminating the effects of the imperfections on the optical density measurements. Higher accuracy in optical density measurements of color patches printed on a web is obtained by identifying any imperfections in the color patches and eliminating the effects of the imperfections on the optical density measurements.

The present invention provides a method for the accurate reflectance and/or optical density measurement of color patches printed on a web. The method includes the steps of using an imaging device to receive light reflected from the printed image on the substrate to produce a signal. The signal is transmitted from the imaging device to a computer and is processed in the computer. The step of processing the signal in the computer includes the steps of digitizing the signal to produce a digitized array of pixels, wherein each pixel has an associated color value, and determining a portion of the pixels within the digitized array corresponding to the color patch. The method further includes the steps of determining an acceptable range of color values for the pixels in the portion of the pixels, determining for each pixel in the portion of pixels whether the color value is within the acceptable range, and computing an aggregate color value for the color patch by averaging the color values of each pixel in the portion of pixels by including only those pixels within the acceptable range.

In operation, an imaging device is positioned to have its field of view on the web. An image within the field of view is illuminated by a light source and the imaging device records an image signal which is a Likeness of the printed image. The light source is synchronized with the web such that the light source is activated when the printed image within the field of view includes a portion of the color bars. The recorded image signal is next digitized by the image capture circuitry and is stored in the computer's memory as a captured image signal array. Various signal processing techniques are utilized to correct the captured image signal array for scattered light, uneven white response across the elements of the imager, black bias, and camera nonlinearities. Additionally, the captured image array is processed to locate the individual color patches. The imperfections in the color patches are identified by tallying all the pixels and calculating the mean and standard deviation. The pixels not within a predetermined range are identified and discarded and are not included in the calculation of optical density. The optical density value for each color patch is then determined. In this manner, the effects of any color patch imperfections on the optical density measurement are eliminated.

DESCRIPTION OF THE PREFERRED EMBODIMENT

Figure 1:
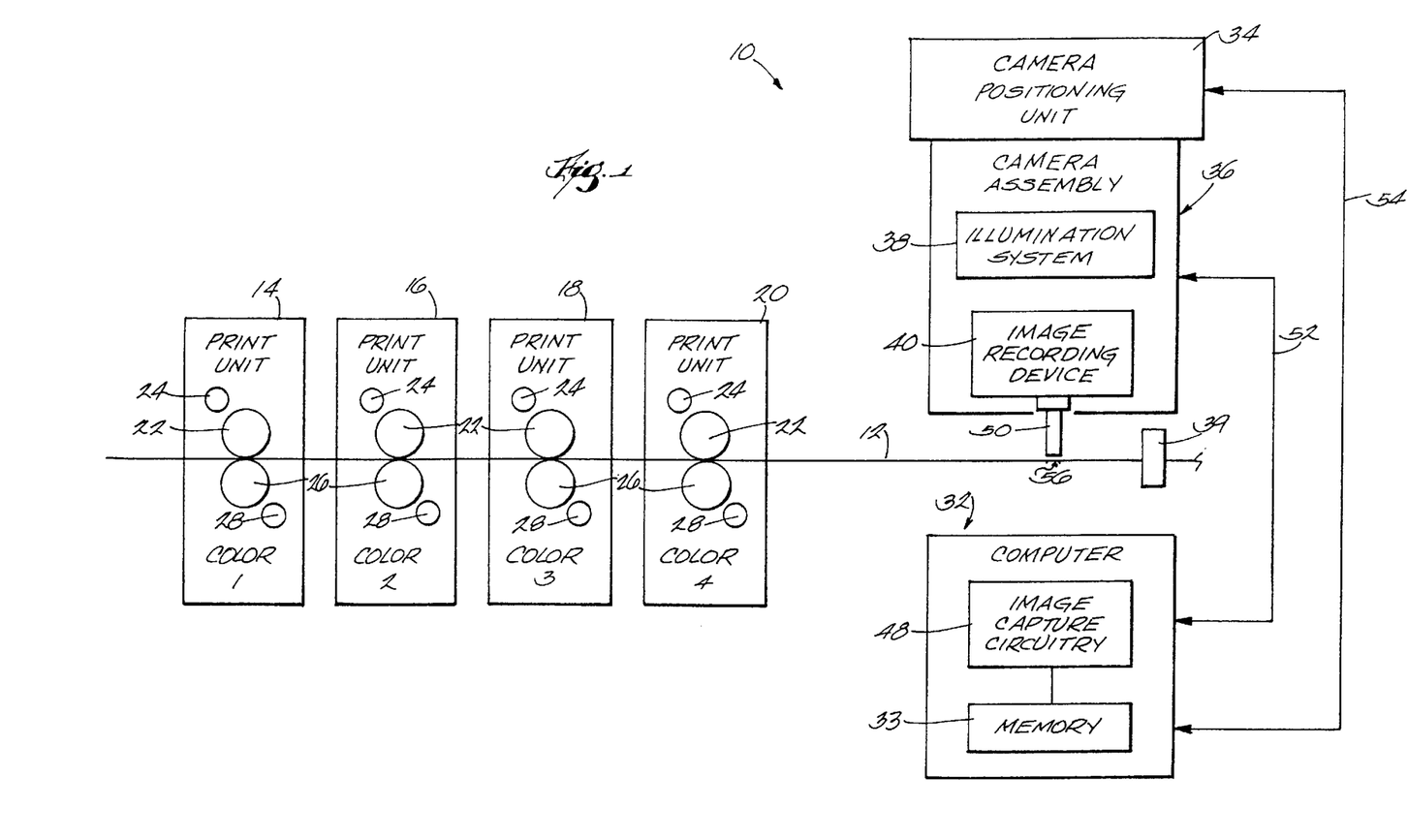
FIG. 1 is a block diagram of a printing system in accordance with the present invention.

Referring to FIG. 1, a printing system 10 for printing a multi-color image upon a web 12 is illustrated. In the preferred embodiment, four printing units 14, 16, 18, and 20 each print one color of the image upon the web 12. This type of printing is commonly referred to as web offset printing. Each printing unit 14, 16, 18, 20 includes an upper blanket cylinder 22, an upper printing plate cylinder 24, a lower blanket cylinder 26, and a lower printing plate cylinder 28. In printing system 10, colors 1, 2, 3, and 4 on units 14, 16, 18, and 20 respectively, are black (K), cyan (C), magenta (M), and yellow (Y). The location of printing units 14, 16, 18, and 20 relative to each other is determined by the printer, and may vary.

In the preferred embodiment, the printing press is a web offset printing press. It is contemplated, however, that the hereinafter described system also be applicable to other types of printing presses, such as rotogravure or flexographic.

The image that is printed on the web 12 includes a color bar 86 (illustrated in FIG. 3) having a plurality of color patches 96. Although the color patches 96 vary in terms of ink colors and tone, each of the color patches 96 has an expected optical density that is uniform across the patch. Referring again to FIG. 1, system 10 also includes a camera assembly 36 in optical communication with the web 12. The camera assembly 36 includes an illumination system 38 and an image recording device 40. Additionally, printing system 10 includes a camera positioning unit 34, a computer 32, and possibly a web stabilizer 39.

In general operation, the camera positioning unit 34 moves the camera assembly 36 to a first position on the web 12. A printed image is illuminated by the illumination system 38 and the image recording device 40 records an image signal which is representative of the printed image within the field of view 56. The illumination system 38 is synchronized with the movement of the web 12 such that the recorded image signal includes a portion of the color bar 86. The computer 32 may be of the conventional type including a 486 or Pentium microprocessor and PC architecture. Computer 32 includes random access memory 33 (semiconductor memory and/or disk drive storage) and image capture circuitry 48 which interfaces with the camera assembly 36.

Computer 32 is connected to camera positioning unit 34 by data bus 54, and computer 32 sends control signals to the camera positioning unit 34. The camera positioning unit 34 is mechanically coupled to camera assembly 36 and moves the camera assembly 36 in a direction perpendicular to the web motion, termed the lateral direction (X-axis, see FIG. 2). The purpose of moving the camera assembly 36 across the web 12 is to allow selective image recording of lateral portions of the printed image on web 12. The camera assembly 36 records the printed image within the field of view 56 for various positions of the camera assembly 36 across the web 12. Web 12 is moving in the Y direction so that circumferential or Y-axis positioning by unit 34 is not necessary because the timing of the strobe light in the illumination system 38 effectively provides circumferential positioning relative to moving web 12.

It is also contemplated that a camera positioning unit 34 not be utilized, if, for example, a plurality of cameras are combined to obtain a field of view that covers all required areas of the web 12, such as all the color patches 96. In the preferred embodiment, the camera assembly 36 is mounted to the press so that measurements can be made on-line. However, it is contemplated that this method can also be used to improve the accuracy of off-line measurements, in which case the camera assembly would not be mounted to the press.

If the web 12 is transparent or translucent, accurate optical density measurements will require that light reflected back through the web 12 be minimized. This can be accomplished by providing a black backing behind the web 12, providing a large open cavity behind the web 12 such that little light will be reflected through the web 12, or utilizing a black roller if the web 12 is stabilized by imaging on a roller.

The camera assembly 36 and camera positioning unit 34 may be mounted on the press anywhere after the ink has been applied to the web 12. For example, in a heatset web offset press, the color measurement system may be mounted between the last print unit and the oven, directly after the oven, on the chill rolls, or after the chill rolls. If optical density measurements are required in the absence of other inks, or if the measurement is required immediately subsequent to printing, it may be advantageous to mount the color measurement system between printing units.

Figure 2:
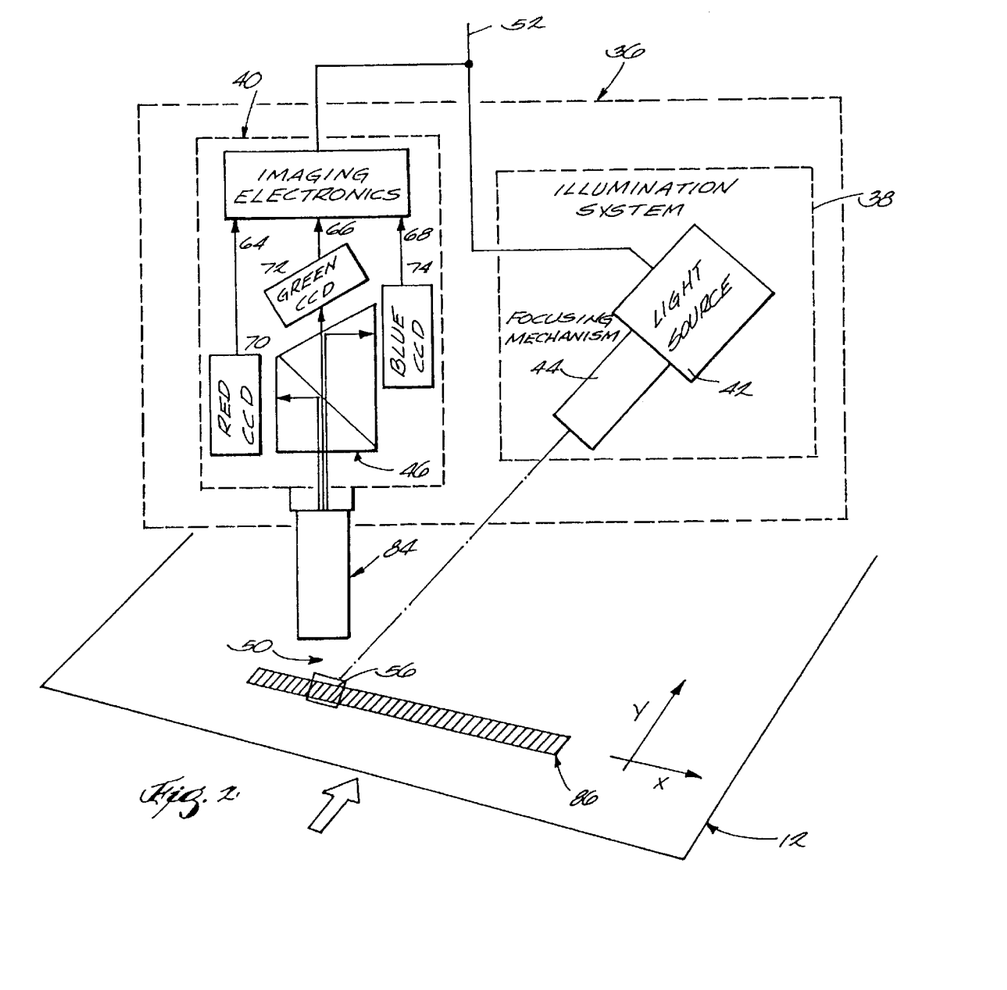
FIG. 2 illustrates a camera assembly and a printed image within the field of view.

In the preferred embodiment, as shown in FIG. 2, the camera assembly 36 includes an image recording device which is a CCD color camera having red (R), green (G), and blue (B) channels. For example, a Sony XC003 3-chip CCD color video camera may be used as the image recording device 40. This camera uses a dichroic prism 46 to separate reflected light from the printed image on the web 12 into a red channel, a green channel, and a blue channel. Each channel includes a separate CCD imager, shown as 70, 72, and 74 respectively. Each of the three channels of the video camera is coupled to the computer 32 via signal bus 52, and each channel is configured to produce a recorded image signal of the printed image within the field of view 56 on web 12. Alternatively, the image recording device could be a multiplicity of light sensors used to sense reflected or transmitted light from a multiplicity of locations, or a single sensor which is scanned in time to sense refected or transmitted light from a multiplicity of locations.

Camera assembly 36 also includes an illumination system 38 which is coupled to computer 32 by signal bus 52. The illumination system 38 includes light source 42 (only one shown) and a focusing mechanism 44. Control signals from the computer 32, corresponding to when the color bar is within the field of view 56, are sent via signal bus 52 to indicate when the web 12 should be illuminated by the light source 42. In the preferred embodiment, pulsed xenon strobe lights with a pulse duration of approximately one microsecond are utilized. With a web speed of approximately 3500 feet per minute and a field of view of roughly 2.0"×1.8", a one microsecond illumination time is preferred to minimize the amount of movement of the printed image during the time the image recording device 40 is quantifying the amount of incoming light reflected from the web 12. By way of example, the light source 42 could include a strobe light assembly utilizing EG&G Strobes FX-199 with power supplies PS-350-1.

The illumination control signals from the computer 32 are produced, for example, by conventional means utilizing rotational position information generated from a sensor placed on one of the blanket cylinders 22, 26, knowledge of the speed of the web 12, and knowledge of the distance between the image recording device 40 and the blanket cylinder 22, 26.

The focusing mechanism 44 efficiently concentrates the light emitted from the light source 42 onto the image within the field of view 56. When the strobe light is flashed, the image recording device 40 records the image within the field of view 56, which contains portions of the color bars.

In the preferred embodiment, the camera 40 is mounted perpendicularly to the web 12 and the field of view 56 preferably is illuminated with two light sources 42 (only one shown) each mounted at an angle of 45 degrees from the camera axis 50. Various specifications for densitometry (for example CIE or ANSI specifications) require the light source be mounted at 45 degrees ±8 degrees from the camera axis 50. A two bulb system may utilize reflectors (not shown) to increase the amount of light emitted from the light source 42 which impinges upon the printed image within the field of view 56.

To minimize the light outside the field of view 56, a baffle (not shown) may be positioned below the light source 42 so the web 12 directly beneath the light source 42 is not illuminated. Additionally, a glare shield (not shown) may be added above the field of view 56 to further reduce unwanted light from entering the system. This effect will occur particularly if the illumination covers an area much larger than the field of view 56.

It is further contemplated that, for some applications with slower web speed, larger fields of view and/or off-line operation, it would not be necessary to use pulsed xenon strobe illumination. Suitable avoidance of blur may be accomplished with the electronic shutter of the camera, or with mechanical shuttering means. In this case, more cost effective lighting may be provided by halogen bulbs.

The variation in brightness from strobe flash to strobe flash may constitute a large source of error in the density calculation. It is contemplated that this variability be reduced by means of a feedback mechanism which disrupts the current to the strobe when a predetermined amount of light has been delivered. This feedback mechanism may consist of a photodetector, an integrator, and a means for disrupting the current to the strobe. Such mechanisms are well known and can be found on commercially available strobe lights for photographic equipment.

The camera assembly 36 preferably is mounted in a light-tight housing to minimize the effects of ambient light on the printed image.

The preferred embodiment of the video camera used in camera assembly 36 includes three CCD imagers 70, 72, 74 each of which provides a resolution of 768 pixels by 494 pixels (X direction by Y direction). A typical CCD imager provides approximately a 4:5 picture aspect ratio such that the field of view of the image recording device will be 2" (x-axis) by 1.8" (y-axis). The image recording device 40 is preferably mounted perpendicularly to the web 12, providing a working distance to the web 12 of approximately six inches. The camera lens 84 in the preferred embodiment is a Sony VCL-16WM 16 mm lens. By way of modification, future developments or different application requirements may make different pixel resolutions, field of view size, and working distance preferable.

The size of the field of view in the preferred embodiment does not make efficient use of the pixels of the detector in that very few of the lines of the image represent color bar information. The efficiency can be improved by use of an imager with an aspect ratio which more closely approximates the aspect ratio of the color bar 86, for example, 768 pixels wide by 256 pixels high. With such an imager, the same amount of information could be derived with less expenditure for computer memory and processing. Alternatively, the use of an anamorphic lens (a lens which has greater magnification in one direction than another) in place of lens 84, would improve pixel efficiency.

Alternatively, a single CCD video camera which has colored filters arranged over each pixel of the image may be used as the image recording device 40. Although this camera is less expensive than a three chip camera, its spatial resolution is not as satisfactory.

Additionally, it is contemplated that cameras having imaging devices other than CCDs may be used. For example, MOS imagers may be used, depending upon the requirements of a particular application.

Referring back to FIG. 1, image capture circuitry 48 includes image capture boards which are connected to the expansion bus of computer 32. By way of example, the image capture circuitry may be of the bus board type manufactured by Synoptics of England SPR4000SCIB with 32 MB RAM which includes an A/D converter, and "Shademaster" diagnostic display driver. The vector signal processing library from Kuck and Associates of Urbana, Ill., may be used to optimize processing speed.

Signal bus 52 transmits recorded image signals from camera assembly 36 to the computer 32, and camera control instructions from computer 32 to camera assembly 36. Image capture circuitry 48 is configured to produce a captured image signal array by converting the recorded image signals into an array of digital signals, of size 640× 480 elements.

Three arrays are generated corresponding to information from each of the three color channels 64, 66, and 68 in FIG. 2. Each captured image signal array element contains an 8-bit "gray value" which is representative of the amount of light reflected from the corresponding area of the printed image within the field of view 56 and onto the corresponding CCD imager. The camera and the image capture boards are calibrated for each channel such that the output of the image converter circuit for a white reference image will have a gray value between 240 and 250 decimal, while a black reference image, with the lens cover on, will have a gray value between 0 and 10 decimal. The captured image signal arrays are stored in memory 33 of computer 32.

Figure 3:
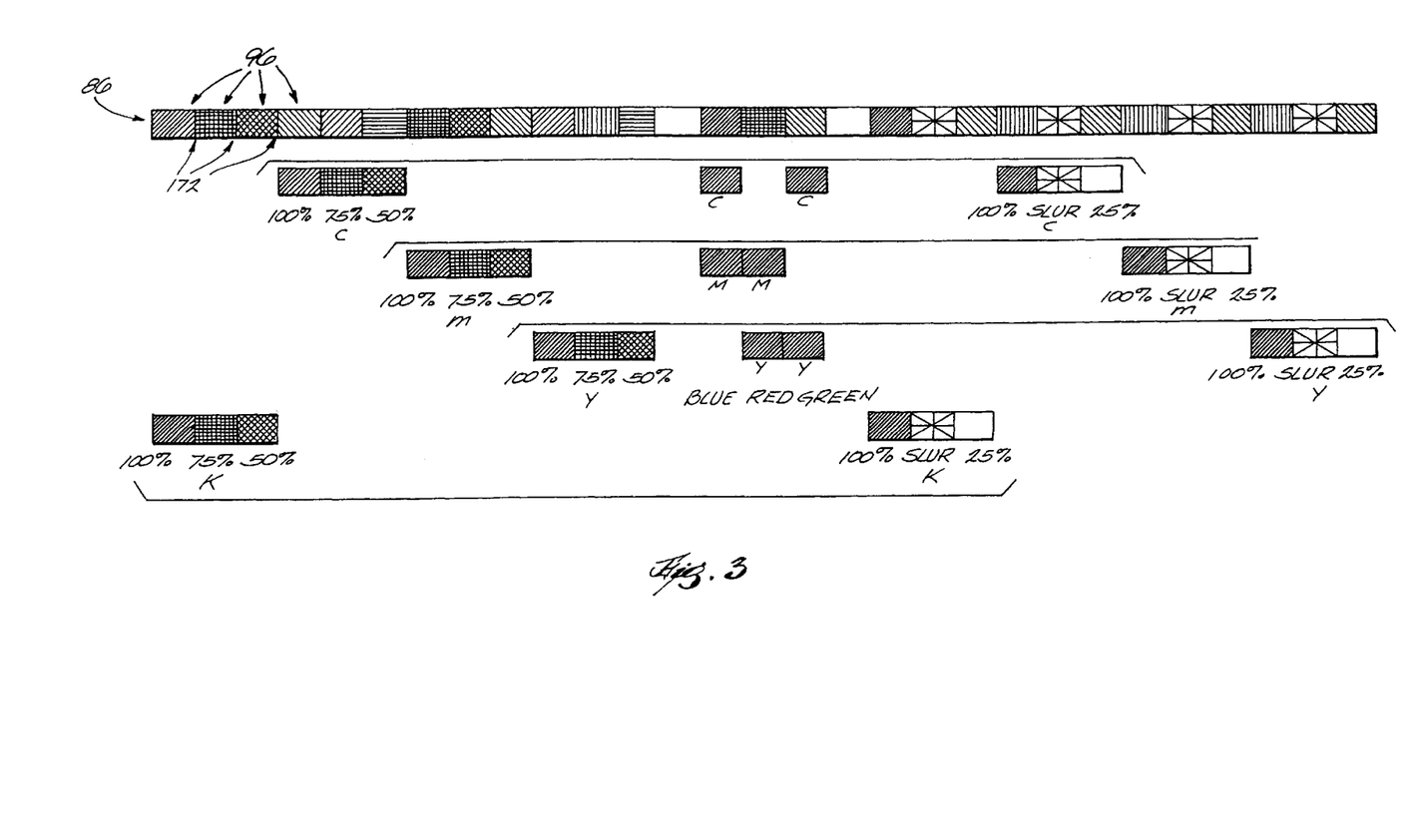
FIG. 3 illustrates a typical color bar.

A representative embodiment of a color bar 86 is shown in FIG. 3. The color patches 96 are arranged side by side in a color bar across the web 12. Typically, the series of color patches illustrated in FIG. 3 is repeated across the width of the web 12. Color bar 86 is comprised of patches of cyan, magenta, yellow, and black components. By way of illustration, color bar 86 may include the following color patches: black 100%, black 75%, black 50%, cyan 100%, cyan 75%, cyan 50%, magenta 100%, magenta 75%, magenta 50%, yellow 100%, yellow 75%, yellow 50%, white, blue, red, green, white, black 100%, black slur, black 25%, cyan 100%, cyan slur, cyan 25%, magenta 100%, magenta slur, magenta 25%, yellow 100%, yellow slur, yellow 25%; where 100% represents full tone of the ink, 50% represents half tone, etc.

By way of example, the field of view 56 may be aligned with the axis of the color bar such that the data representing the color bar in the captured image signal array is located in adjacent rows of the captured image signal array. In this orientation, lateral direction on the web is aligned with the X direction of the camera and the circumferential direction on the web is aligned with the Y direction of the camera. As illustrated in FIG. 2, the field of view 56 may contain only a portion of the color bar 86.

In the preferred embodiment, the size of the field of view is 2.0"×1.8". Multiple considerations go into the selection of the size of the field of view. The first consideration is the size of the color patches 96. The field of view must be small enough such that each individual color patch consists of multiple elements of the captured image signal array. This allows for multiple elements to be averaged and also allows for elements near the boundaries of the color patch to be disregarded. The second consideration is the pixel resolution of the camera. Increased camera resolution will allow for more pixels in the same field of view. A third consideration is the avoidance of moiré patterns between the CCD pixels and the halftone dots in the printed color bars. For any set of conditions of pixel resolution and halftone dot spacing, there will be a range for the field of view which should be avoided.

Figure 4:
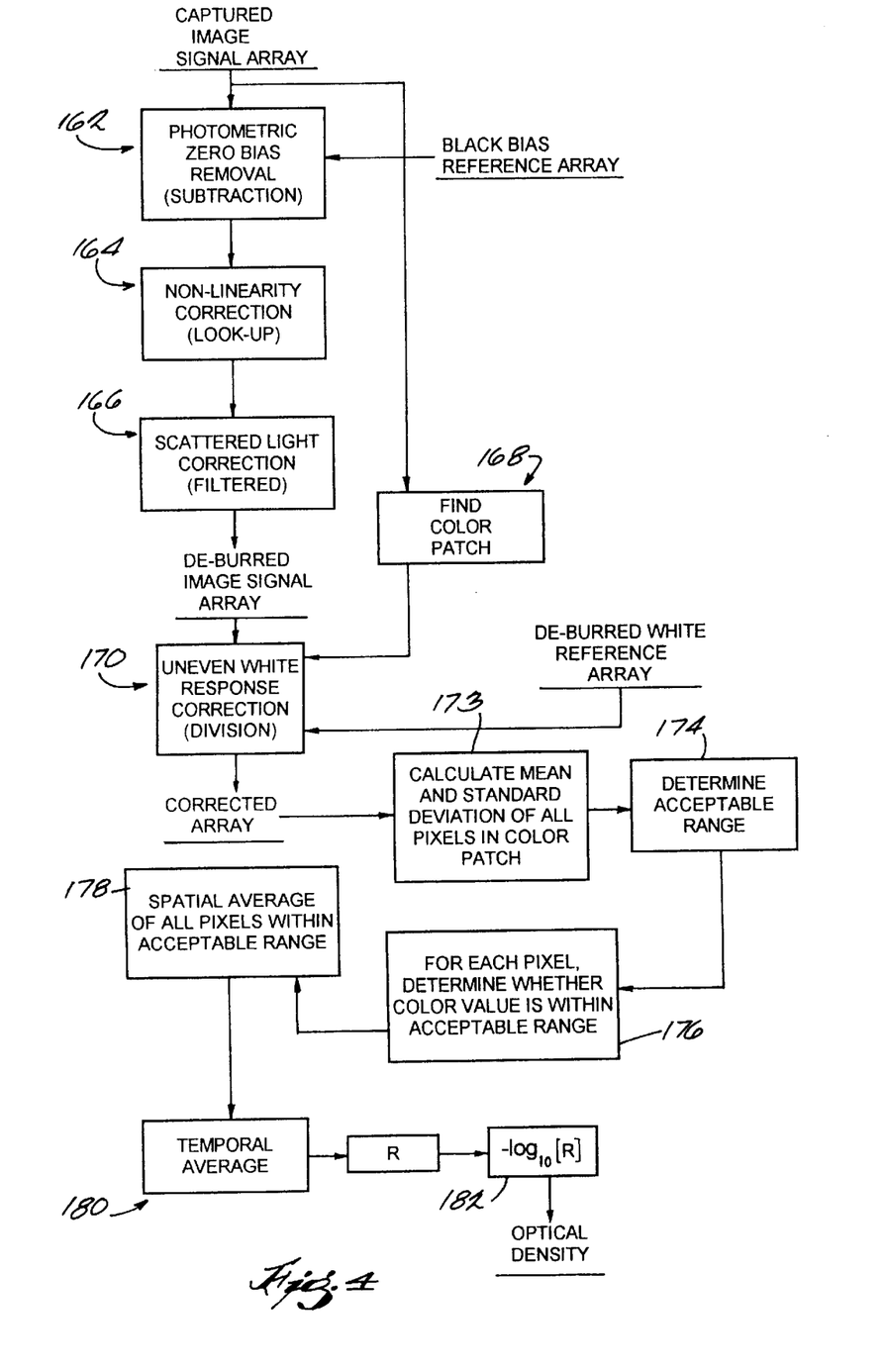
FIG. 4 is a flow chart of computations performed on the captured image signal array to the obtain optical density of a color patch.

Computer 32 operates as a processing circuit, as shown in FIG. 4, to manipulate the captured image signal array for each color channel. Each captured image signal array is corrected for photometric zero at step 162 by subtracting a black bias reference array. The array is also corrected for system nonlinearities at step 164, scattered light at step 166 to produce a de-blurred image signal array.

The correction for photometric zero, correction for system nonlinearities, and scattered light correction is disclosed in U.S. Pat. No. 5,724,259, which is hereby incorporated by reference.

At step 168, the captured image signal array is processed to locate the color patch boundaries within the captured image signal array. Each pixel of the captured image signal array represents color information for the image within the field of view of the camera assembly. However, because the size of an individual color patch 96 is small compared to the field of view, in order to extract the color information associated with each individual color patch, it is necessary to locate each color patch 96 within the array. In the preferred embodiment, the size of the captured image signal array is 640 by 480 pixels, while the size of the color patch corresponds to approximately 20×15 pixels.

As set forth above, the field of view 56 of the camera assembly 40 is aligned with the axis of the color bar 86 such that the data representing the color bar in the captured image signal array is located in adjacent rows of the captured image signal array. The captured image signal array contains a portion of the color bar 86, which extends laterally across the web 12. The exact positioning of the color bar 86 within the field of view 56, however, is not known, because of web weave (movement of the web along the X-axis), circumferential (Y-axis) motion of web, and misalignment between colors. Thus, the rows of the captured image signal array in which the color bar data may be found, are not known. Similarly, the columns of the captured array in which the individual color patches may be found are not known. Therefore, the computer 32 is programmed to operate as a color patch location circuit, providing information regarding color patch boundaries 172 in the captured image signal array.

The color bar determination circuit has three major steps:
1. identification of rows in the captured image signal array which correspond to the color bar 86,
2. identification of the top and bottom rows of the color bar 86, and
3. identification of each color patch edge 172.

The color bar determination circuit operates as disclosed in U.S. Pat. No. 5,724,259.

The color patch location determination is repeated to locate each of the color patches in the color bar 86. In the preferred embodiment, the uncorrected captured image signal array is used to determine the boundaries of each color patch in the color bar.

Computer 32 is also programmed to operate as an uneven white response correction circuit at step 170. This correction involves dividing, element by element, the filtered image signal array by a filtered white reference array to produce a corrected array for each individual color patch. This correction is also disclosed in U.S. Pat. No. 5,724,259.

Note that the location of each color patch within the captured image signal array has been determined at this point. To minimize computations, uneven white response correction need only be performed on the relevant color patch elements of the filter corrected image signal array.

It is also contemplated that the order of corrections may be varied. For example, the process to find the individual color patches within an array may be performed on the filtered image signal array instead of on the uncorrected captured image signal array. The black bias reference array and/or the white reference array may be decimated over a plurality of elements such that fewer data points need be stored. The black bias reference array and/or white reference array may be generated by frame averaging over time several captured black reference arrays. It is also contemplated that some corrections may not be necessary for the level of required accuracy.

Computer 32 is also programmed to operate to identify imperfections in the color patches and to eliminate the effects of the imperfections on the calculated optical density value for each color patch. This involves calculating the mean value and standard deviation of the reflectance values associated with all pixels within the horizontal and vertical bounds of the color patch at step 173.

At step 174, the mean and standard deviation are used to compute an acceptable color value range, in this case a reflectance range. At step 176, for each pixel, a determination is made whether the color value is within the acceptable range. Valid pixels are those pixels having reflectance values within the range, and invalid pixels are those pixels having reflectance values outside of the range.

By way of example, all pixels within ± two standard deviation units (±2.0 s) of the mean may be considered valid and are included in the calculation of color value. The ideal selected range (of standard deviation units) may also depend upon the type of patch. In the preferred embodiment, a pixel value in a solid patch is allowed only if the pixel value is within ±1.75 s; a pixel value in a 75% patch is allowed if the pixel value is within ±2.0 s; a pixel value in a 50% patch is allowed if the pixel value is within ±2.25 s; and a pixel value in a 25% patch is allowed if the pixel value is within ±2.5 s. A pixel value of the solid overprint patches (i.e., red, green and blue) is acceptable if the value is ±1.75 s in their dominant channels, and ±2.0 s in the remaining two color channels. A pixel value in a white reference patch is acceptable if the value is ±2.5 s. The precise tolerance values described herein may be adjusted according to the characteristics of the print being measured, and according to the characteristics of the measuring device.

If the pixel's color value is not within the range, the pixel is discarded from further computations. If the pixel's color value is within the range, the pixel is included in the computation of color value. The pixel color values can be compared against a range determined for each of the three channels of the camera (red, green, and blue). The pixel is valid only if its color value is within the selected range in all channels. Alternatively, the pixel color values may be compared against the selected range just for the complimentary color of the patch (e.g., the red channel for a cyan color patch). However, the former method is more robust, particularly in finding colored blemishes.

At step 178, a spatial average of the color values of all the pixels within the acceptable range is determined. Optionally, temporal averaging at step 180 may also be performed by obtaining several frames from the camera and averaging the color values computed for corresponding patches. In the preferred embodiment, the color value obtained after step 180 is reflectance.

Finally, optical density D may be calculated as −log[R] for each of the color patches at step 182. The densities thus arrived at may be used further in conventional computation. For example, the solid ink density and the density of the corresponding 50% patch are together used to compute dot gain; the solid ink density and the density of the corresponding 75% patch are together used to compute print contrast; the solid ink density of an overprint and the corresponding solid ink density are used to compute trap. Together with solid ink density, the dot gain, print contrast and trap may be used for quality control of the print run, for diagnosis of printing conditions or for control of inking levels.

Although the preferred embodiment has been described, alternative embodiments are contemplated. For example, in the calculation of color value at step 178, the elimination of one or more pixels may have an appreciable effect on the value of the mean and standard deviation of the whole set of pixels. In an alternative embodiment, repeated application can be made of the rejection of pixels outside of the range until all the pixels are within (for example) ±3.0 s of the mean. This may be performed by eliminating all pixels outside the range at each step, in which case it may be necessary to limit the number of elimination steps to two or three to avoid over-elimination. It may be preferable, however, to eliminate one pixel at a time, and recalculate the range after each single pixel elimination.

In the above-described embodiments, potentially useful information is not utilized. For example, the location of a pixel with respect to other pixels outside the selected range is not considered, nor is the total number of pixels within the color patch, or the location of the pixel with respect to the edge of the patch. Use of this information could increase the accuracy of the color value determination.

By way of example, this information could be employed in the method by an additional step in which all the pixels which are adjacent to pixels determined to be outside the range are screened against a second, tighter range. Pixels adjacent to pixels determined to be outside the range and which are outside this tightened range would also be considered invalid and hence excluded from the aggregate color value determination.

One skilled in the art will also recognize that the confidence in the estimation of standard deviation is improved with a larger sample size. Thus, if only a smaller number of pixels are available, it would be advantageous to widen the acceptance range. For a more complete treatment, see Snedecor and Cochran, *Statistical Methods*, copyright 1980, Iowa State University Press, section 15.4.

The preceding methods implicitly assume that the fluctuations in pixel color values are normally distributed. In the event that the pixel color values are shown to have distributions other than normal, the criteria for acceptance may be changed to reflect the more appropriate distribution. By way of example, at extremely low light levels, the Poisson distribution may be a more accurate depiction of the distribution of pixel intensities. This distribution is not symmetric, as is the normal distribution, but is skewed. Setting an acceptance range which is symmetric would lead to a biased estimate of the mean, because statistically legitimate data points which are above the mean may be excluded.

Alternative, so-called "robust" methods exist for the estimation of the mean in step 173. These include obtaining the median of the pixel color values and Tukey's trimean. The median is the pixel value at which exactly half the pixel values are greater and half the pixel values are smaller, which is to say, the 50th percentile. Tukey's trimean is a weighted average of the 25th percentile, the median, and the 75th percentile, with weightings of 0.25, 0.5, and 0.25. To one skilled in the art, other linear combinations of the order statistics will be an obvious extension.

In the event that the printing substrate (generally paper) is not entirely opaque, the edge of a patch next to an area without ink cover will not exhibit as strong a color as the interior of the patch. In this case, a more accurate measurement will be made by excluding these border pixels. The excluded border, for example, may be the width of two pixels, depending on the substrate and pixel resolution.

There are many sources of variation which contribute to the magnitude of the computed standard deviation. These include imperfections, paper grain, uneven inking, and measurement noise. For halftone patches, there is an additional source of variation caused by the difference in reflectance between halftone dots and the space between them. If halftones are the majority of the variation, then the distribution of pixel values will be platykurtic and a fewer number of pixels will be expected in the tails. Furthermore, pixels in the center of a halftone dot or midway between halftone dots may be preferentially rejected. This is undesirable, because the total color effect should include all the pixels, rejecting based only on imperfections.

One means of avoiding this is to establish a template for each halftone cell, which indicates which areas should be darker and which should be lighter. This template is subtracted, on a pixel by pixel basis from the patch that is to be measured, and this difference patch is used to determine acceptance and rejection of pixels. The template can either be established as an idealized image, from pre-press information, or by taking an aggregate of on-press images.

The system herein described is adequate for measurement of color on a single side of a web. In many applications, color measurement must be performed on both sides of a web. The invention described may be adapted to measure color on two sides of the web by replication of the entire system, by replication of the camera assembly above and below the web and the addition of a video multiplexer before the image capture circuitry, or by providing a camera positioning unit which is capable of positioning the camera assembly on either side of the web.

What is claimed is:

1. A method for monitoring the color quality of a printed image printed on a web, the printed image including at least one color patch, the method comprising the steps of:

using an imaging device to receive light reflected from the printed image on the substrate and to produce a signal;

transmitting the signal from the imaging device to a computer; and processing the signal in the computer, the step of processing the signal in the computer including the steps of digitizing the signal to produce a digitized array of pixels, each pixel having an associated color value, determining a plurality of the pixels within the digitized array corresponding to the color patch, determining the mean and standard deviation of the color values for the plurality of pixels within the digitized array corresponding to the color patch, using the mean and standard deviation to calculate an acceptable range of color values for the plurality of pixels, determining for each pixel in the plurality of pixels whether the color value is within the acceptable range, and computing an aggregate color value for the color patch by averaging the color values of the pixels in the plurality of pixels, including only those pixels having color values within the acceptable range in the determination of the color quality of the color patch.

2. The method as recited in claim 1, wherein the color value is optical density or reflectance.

3. The method as recited in claim 1, wherein the step of determining an acceptable range of color values includes calculating the mean and standard deviation of the associated color values of all the pixels in the portion of the pixels.

4. The method as recited in claim 1, wherein determining a portion of the pixels within the digitized array corresponding to the color patch includes (a) identifying at least one row which is part of the color patch; (b) identifying the top and bottom rows of the color patch; and (c) determining the edges of the color patch.

5. The method as recited in claim 1, wherein the step of processing the signal in the computer includes the step of correcting the digitized array of pixels for photometric zero.

6. The method as recited in claim 1, wherein the step of processing the signal in the computer includes the step of correcting the digitized array of pixels for scattered light.

7. The method as recited in claim 1, wherein the step of processing the signal in the computer includes the step of correcting the digitized array for uneven white response.

8. The method as recited in claim 1, wherein the color value is optical density or reflectance.

9. The method as recited in claim 1, wherein the step of calculating an acceptable range includes determining a range centered around the mean.

10. A method for monitoring the color quality of a printed image printed on a web, the printed image including at least one color patch, the method comprising the steps of:

using an imaging device to receive light reflected from the printed image on the substrate and to produce a signal;

transmitting the signal from the imaging device to a computer; and processing the signal in the computer, the step of processing the signal in the computer including the steps of digitizing the signal to produce a digitized array of pixels, each pixel having an associated color value, determining a portion of the pixels within the digitized array corresponding to the color patch, determining a first acceptable range of color values for the pixels in the portion of the pixels, determining a first group of pixels that have color values outside the first acceptable range, determining a second acceptable range of color values for the pixels adjacent to pixels having color values outside the first acceptable range, determining a second group of pixels from the pixels adjacent to pixels having color values outside the first acceptable range that have color values outside the second acceptable range, and computing an aggregate color value for the color patch by averaging the color values of each pixel in the portion of pixels excluding the first group of pixels and the second group of pixels.

11. A method for monitoring the color quality of a printed image printed on a web, the printed image including at least one color patch including halftones, the method comprising the steps of:

using an imaging device to receive light reflected from the printed image on the substrate and to produce a signal;

transmitting the signal from the imaging device to a computer;

establishing a template for the color patch, the template having pixels with expected color values; and processing the signal in the computer, the step of processing the signal in the computer including the steps of digitizing the signal to produce a digitized array of pixels, each pixel having an associated measured color value, determining a portion of the pixels within the digitized array corresponding to the color patch, subtracting the measured color values from the expected color values on a pixel by pixel basis to obtain a difference array for the portion of the pixels corresponding to the color patch, determining an acceptable range of color values for the difference array, determining for each pixel in the portion of pixels whether the color value is within the acceptable range, and computing an aggregate color value for the color patch by averaging the color values of each pixel in the portion of pixels including only those pixels having color values within the acceptable range.

12. A method for monitoring the color quality of a printed image printed on a web, the printed image including at least one color patch, the method comprising:

using an imaging device to receive light reflected from the printed image on the substrate and to produce a signal; and processing the signal to produce a digitized array of pixels, each pixel having an associated color value, determining a plurality pixels within the digitized array corresponding to the color patch, determining the mean and standard deviation of the color values for the plurality of the pixels within the digitized array corresponding to the color patch, using the mean and standard deviation to calculate an acceptable range of color values based on the color values of all the pixels in the plurality of the pixels, determining for each pixel in the plurality of pixels whether the color value is within the acceptable range, and computing an aggregate color value for the color patch by averaging the color values of the pixels in the plurality of pixels including only those pixels having color values within the acceptable range in the determination of the color quality of the color patch.

13. The method as recited in claim 12, wherein the color value is optical density or reflectance.

14. The method as recited in claim 12, wherein determining a portion of the pixels within the digitized array corresponding to the color patch includes (a) identifying at least one row which is part of the color patch; (b) identifying the top and bottom rows of the color patch; and (c) determining the edges of the color patch.

* * * * *